US012017116B2

(12) United States Patent
Kim et al.

(10) Patent No.: US 12,017,116 B2
(45) Date of Patent: Jun. 25, 2024

(54) APPARATUS AND METHOD FOR EVALUATING HUMAN MOTION USING MOBILE ROBOT

(71) Applicant: ELECTRONICS AND TELECOMMUNICATIONS RESEARCH INSTITUTE, Daejeon (KR)

(72) Inventors: Do-Hyung Kim, Daejeon (KR); Jae-Hong Kim, Daejeon (KR); Young-Woo Yoon, Daejeon (KR); Jae-Yeon Lee, Daejeon (KR); Min-Su Jang, Daejeon (KR); Jeong-Dan Choi, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 798 days.

(21) Appl. No.: 17/106,465

(22) Filed: Nov. 30, 2020

(65) Prior Publication Data
US 2021/0394021 A1  Dec. 23, 2021

(30) Foreign Application Priority Data
Jun. 23, 2020 (KR) .......................... 10-2020-0076499
Oct. 28, 2020 (KR) .......................... 10-2020-0141426

(51) Int. Cl.
*A63B 24/00* (2006.01)
*A61B 5/11* (2006.01)
(Continued)

(52) U.S. Cl.
CPC ........ *A63B 24/0062* (2013.01); *A61B 5/1116* (2013.01); *A61B 5/1128* (2013.01);
(Continued)

(58) Field of Classification Search
CPC .......... A63B 24/0062; A63B 2220/806; A63B 2230/62; G06T 7/246; G06T 7/73;
(Continued)

(56) References Cited

U.S. PATENT DOCUMENTS

2018/0253108 A1\* 9/2018 Heinla ................. G05D 1/0274
2019/0362139 A1   11/2019 Mehl et al.
(Continued)

FOREIGN PATENT DOCUMENTS

JP       2016-80671        5/2016
KR  10-2019-0081738        7/2019
(Continued)

*Primary Examiner* — Joseph L Greene
(74) *Attorney, Agent, or Firm* — KILE PARK REED & HOUTTEMAN PLLC

(57) ABSTRACT

Disclosed herein are an apparatus and method for evaluating a human motion using a mobile robot. The method may include identifying the exercise motion of a user by analyzing an image of the entire body of the user captured using a camera installed in the mobile robot, evaluating the pose of the user by comparing the standard pose of the identified exercise motion with images of the entire body of the user captured by the camera of the mobile robot from two or more target locations, and comprehensively evaluating the exercise motion of the user based on the pose evaluation information of the user from each of the two or more target locations.

18 Claims, 11 Drawing Sheets

(51) Int. Cl.
*B25J 19/02* (2006.01)
*G06T 7/246* (2017.01)
*G06T 7/73* (2017.01)

(52) U.S. Cl.
CPC .............. *B25J 19/023* (2013.01); *G06T 7/246* (2017.01); *G06T 7/73* (2017.01); *A63B 2220/806* (2013.01); *A63B 2230/62* (2013.01); *G06T 2207/30196* (2013.01)

(58) Field of Classification Search
CPC ......... G06T 2207/30196; A61B 5/1116; A61B 5/1128; B25J 19/023
See application file for complete search history.

(56) References Cited

U.S. PATENT DOCUMENTS

| | | | |
|---|---|---|---|
| 2019/0362506 A1* | 11/2019 | Leroyer | G06T 7/97 |
| 2020/0311429 A1* | 10/2020 | Chen | A61B 5/1116 |
| 2021/0279475 A1* | 9/2021 | Tusch | H04L 63/0861 |
| 2021/0374975 A1* | 12/2021 | Shoeb | B64C 39/024 |
| 2021/0382544 A1* | 12/2021 | Butcher | G06V 40/20 |
| 2022/0092814 A1* | 3/2022 | Eberspach | G06T 7/521 |
| 2022/0108468 A1* | 4/2022 | Nakamura | G06V 40/103 |
| 2022/0351405 A1* | 11/2022 | Zhou | G06F 3/01 |
| 2023/0120124 A1* | 4/2023 | Melzer | A63F 13/211 |
| | | | 434/258 |

FOREIGN PATENT DOCUMENTS

| | | |
|---|---|---|
| KR | 10-2020-0022788 | 3/2020 |
| KR | 10-2021-0028375 | 3/2021 |

* cited by examiner

APPARATUS AND METHOD FOR EVALUATING HUMAN MOTION USING MOBILE ROBOT

CROSS REFERENCE TO RELATED APPLICATIONS

This application claims the benefit of Korean Patent Application No. 10-2020-0076499, filed Jun. 23, 2020, and No. 10-2020-0141426, filed Oct. 28, 2020, which are hereby incorporated by reference in their entireties into this application.

BACKGROUND OF THE INVENTION

1. Technical Field

The disclosed embodiment relates to technology for enabling a robot living with a human to evaluate human exercise motions, such as fitness training, yoga, stretching, and the like, based on image analysis.

2. Description of the Related Art

At-home workouts (home training), that is, doing exercise alone at home while watching video using a TV or smartphone, has become very popular and is emerging as a trend. Recently, commercial products for recognizing exercise positions of a learner using a camera and thereby evaluating and correcting the exercise positions in real time using Artificial-Intelligence (AI) technology have been released. An AI coaching service based on such motion evaluation is expected to spread to various fields, such as those of fitness, dieting, professional sports, medical rehabilitation, and the like, and markets related thereto are expected to grow rapidly.

The core technology in the AI coaching service based on image analysis is pose information extraction technology for detecting the pose of a learner. Most conventional technologies detect human joint positions and use skeletal information formed of information about the detected joints as the pose information of a learner. Therefore, it is very important to accurately detect the positions of joints, and the accuracy of detection of joint positions greatly affects the performance of a comprehensive motion evaluation system.

However, existing technologies for evaluating human motion using a camera attached to a TV or smartphone are not capable of accurately detecting all of the joints that are important for motion evaluation. Accordingly, there is a problem in that a reliable evaluation result cannot be provided to users. That is, depending on the motion, there is an optimal camera orientation for facilitating detection of the position of each joint, and thus a fixed camera location is only limitedly able to accurately detect all of the joints. Also, when a specific joint is hidden by other body parts or objects, it is difficult to accurately detect the position of the joint. Therefore, the conventional technologies provide only a partial evaluation result by comparing and evaluating only some joints, the positions of which are capable of being detected.

In order to overcome the limitations of a single camera, an attempt has been made to solve this problem using multiple cameras (e.g., two to four cameras). However, this incurs other problems, in which installation costs are increased and in which it is necessary to configure a separate system including the multiple cameras. Also, although multiple cameras are advantageous for detecting the positions of joints, there is still a problem in that it is difficult to actively move to the optimal orientation that is advantageous for the detection of each joint, because the multiple cameras are fixed.

DOCUMENTS OF RELATED ART (Patent Document 1) Korean Patent Application Publication No. 10-2020-0022788

SUMMARY OF THE INVENTION

An object of the disclosed embodiment is to enable a robot to observe a human motion from the optimal location by changing the location thereof when a human performs the motion, thereby improving the performance of evaluation of a pose or motion.

A method for evaluating a human motion using a mobile robot according to an embodiment may include identifying an exercise motion of a user by analyzing an image of the entire body of the user captured using a camera installed in the mobile robot; evaluating the pose of the user by comparing a standard pose of the identified exercise motion with images of the entire body of the user captured by the camera of the mobile robot from two or more target locations; and comprehensively evaluating the exercise motion of the user based on pose evaluation information of the user from each of the two or more target locations.

Here, evaluating the pose of the user may include detecting a joint in the images of the entire body of the user; and calculating a pose accuracy score for a body segment formed of joints, the detection accuracy value of which is equal to or greater than a threshold.

Here, evaluating the pose of the user may further include recording the detection accuracy value of the joint and the pose accuracy score for the body segment in a pose evaluation chart, and in the pose evaluation chart, all of body segments and joints of the user may be marked.

Here, evaluating the pose of the user may be configured to repeatedly evaluate each body segment, and recording the detection accuracy value and the pose accuracy score may be configured to record the number of times the body segment is evaluated in the pose evaluation chart using a color or brightness such that the number of times is identified according to the color or brightness.

Here, evaluating the pose of the user may be configured to set the target locations based on a pose profile. When the pose profile includes a weight and a 2D direction vector for each body segment, the body segment to be observed next may be selected in order of weight, and the target location, which is an optimal location from which to observe the selected body segment, may be set based on the 2D direction vector of the selected body segment.

Here, evaluating the pose of the user may be configured to set the target locations based on a pose profile. When the pose profile includes only a weight for each body segment, the body segment to be observed next may be selected in order of weight, the target location, which is an optimal location from which to observe the selected body segment, may be calculated in real time, and the target location may be set to a point from which two joints forming the selected body segment are capable of being observed and at which distances from the two joints are equal to each other, the point being extended from the center of the body segment so as to be perpendicular to the body segment.

Here, evaluating the pose of the user may be configured such that, when no pose profile is provided, the target location is set while moving to points at a fixed distance from the user by a fixed angle.

Here, evaluating the exercise motion of the user may include calculating the detection accuracy value of a body segment using the average of detection accuracy values of joints forming the body segment; calculating the final pose accuracy score of the body segment using a body segment detection accuracy score and the average of the detection accuracy values of the body segment; and calculating a final motion accuracy based on the final pose accuracy score and the weight of each body segment.

An apparatus for evaluating a human motion using a mobile robot according to an embodiment may include memory in which at least one program is recorded; and a processor for executing the program. The program may perform identifying an exercise motion of a user by analyzing an image of the entire body of the user captured using a camera installed in the mobile robot; evaluating the pose of the user by comparing a standard pose of the identified exercise motion with images of the entire body of the user captured by the camera of the mobile robot from two or more target locations; and comprehensively evaluating the exercise motion of the user based on pose evaluation information of the user from each of the two or more target locations.

Here, evaluating the pose of the user may include detecting a joint in the images of the entire body of the user; and calculating a pose accuracy score for a body segment formed of joints, the detection accuracy value of which is equal to or greater than a threshold.

Here, evaluating the pose of the user may further include recording the detection accuracy value of the joint and the pose accuracy score for the body segment in a pose evaluation chart, and in the pose evaluation chart, all of body segments and joints of the user may be marked.

Here, evaluating the pose of the user may be configured to repeatedly evaluate each body segment, and recording the detection accuracy value and the pose accuracy score may be configured to record the number of times the body segment is evaluated in the pose evaluation chart using a color or brightness such that the number of times is identified according to the color or brightness.

Here, evaluating the pose of the user may be configured to set the target locations based on a pose profile. When the pose profile includes a weight and a 2D direction vector for each body segment, the body segment to be observed next may be selected in order of weight, and the target location, which is an optimal location from which to observe the selected body segment, may be set based on the 2D direction vector of the selected body segment.

Here, evaluating the pose of the user may be configured to set the target locations based on a pose profile. When the pose profile includes only a weight for each body segment, the body segment to be observed next may be selected in order of weight, the target location, which is an optimal location from which to observe the selected body segment, may be calculated in real time, and the target location may be set to a point from which two joints forming the selected body segment are capable of being observed and at which distances from the two joints are equal to each other, the point being extended from the center of the body segment so as to be perpendicular to the body segment.

Here, evaluating the pose of the user may be configured such that, when no pose profile is provided, the target location is set while moving to points at a fixed distance from the user by a fixed angle.

Here, evaluating the exercise motion of the user may include calculating the detection accuracy value of a body segment using the average of detection accuracy values of joints forming the body segment; calculating the final pose accuracy score of the body segment using a body segment detection accuracy score and the average of the detection accuracy values of the body segment; and calculating a final motion accuracy based on the final pose accuracy score and the weight of each body segment.

A method for evaluating a human motion using a mobile robot according to an embodiment may include identifying an exercise motion of a user by analyzing an image of the entire body of the user captured using a camera installed in the mobile robot; detecting a standard pose and a pose profile of the identified exercise motion; setting a target location based on the pose profile; evaluating the pose of the user by comparing the standard pose with an image of the entire body of the user that is captured by the camera after the mobile robot moves to the set target location; and comprehensively evaluating the exercise motion of the user based on pose evaluation information of the user from each of the target locations. Here, setting the target location and evaluating the pose of the user may be repeatedly performed.

Here, evaluating the pose of the user may include detecting a joint in the image of the entire body of the user; and repeatedly calculating a pose accuracy score for a body segment formed of joints, the detection accuracy value of which is equal to or greater than a threshold, as many times as a predetermined evaluation number.

Here, setting the target location may be configured to set the target location based on the pose profile. When the pose profile includes a weight and a 2D direction vector for each body segment, the body segment to be observed next may be selected in order of weight, and the target location, which is an optimal location from which to observe the selected body segment, may be set based on the 2D direction vector of the selected body segment.

Here, setting the target location may be configured to set the target location based on the pose profile. When the pose profile includes only a weight for each body segment, the body segment to be observed next may be selected in order of weight, the target location, which is an optimal location from which to observe the selected body segment, may be calculated in real time, and the target location may be set to a point from which two joints forming the selected body segment are capable of being observed and at which distances from the two joints are equal to each other, the point being extended from the center of the body segment so as to be perpendicular to the body segment.

BRIEF DESCRIPTION OF THE DRAWINGS

The above and other objects, features and advantages of the present invention will be more clearly understood from the following detailed description, taken in conjunction with the accompanying drawings, in which.

DESCRIPTION OF THE PREFERRED EMBODIMENTS

Figure 1:
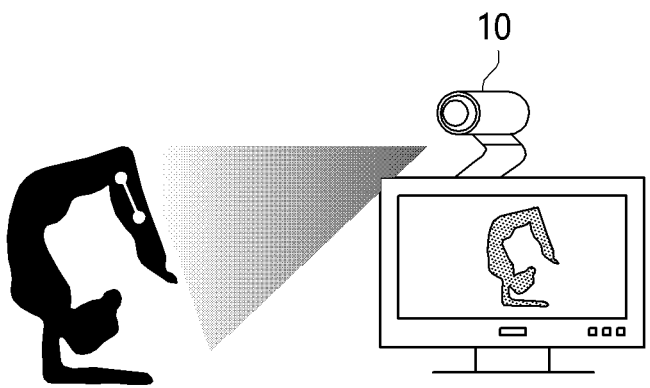
FIG. 1 is a concept diagram for an apparatus for evaluating a human pose using a fixed camera.
Figure 1:
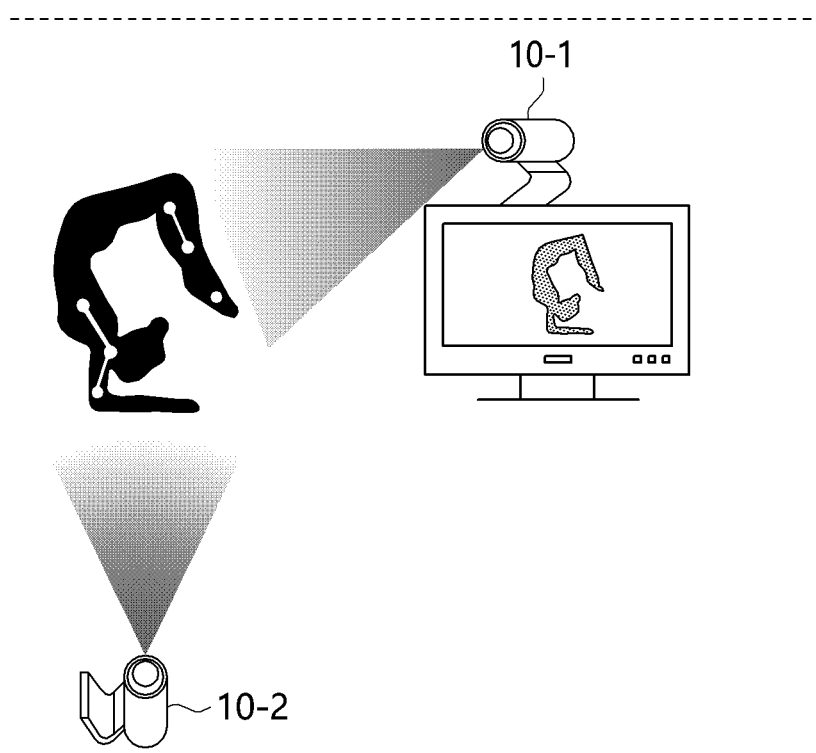

The advantages and features of the present invention and methods of achieving the same will be apparent from the exemplary embodiments to be described below in more detail with reference to the accompanying drawings. However, it should be noted that the present invention is not limited to the following exemplary embodiments, and may be implemented in various forms. Accordingly, the exemplary embodiments are provided only to disclose the present invention and to let those skilled in the art know the category of the present invention, and the present invention is to be defined based only on the claims. The same reference numerals or the same reference designators denote the same elements throughout the specification.

It will be understood that, although the terms "first," "second," etc. may be used herein to describe various elements, these elements are not intended to be limited by these terms. These terms are only used to distinguish one element from another element. For example, a first element discussed below could be referred to as a second element without departing from the technical spirit of the present invention.

The terms used herein are for the purpose of describing particular embodiments only and are not intended to limit the present invention. As used herein, the singular forms are intended to include the plural forms as well, unless the context clearly indicates otherwise. It will be further understood that the terms "comprises," "comprising,", "includes" and/or "including," when used herein, specify the presence of stated features, integers, steps, operations, elements, and/or components, but do not preclude the presence or addition of one or more other features, integers, steps, operations, elements, components, and/or groups thereof.

Unless differently defined, all terms used herein, including technical or scientific terms, have the same meanings as terms generally understood by those skilled in the art to which the present invention pertains. Terms identical to those defined in generally used dictionaries should be interpreted as having meanings identical to contextual meanings of the related art, and are not to be interpreted as having ideal or excessively formal meanings unless they are definitively defined in the present specification.

Hereinafter, an apparatus and method for evaluating a human pose using a mobile robot according to an embodiment will be described in detail with reference to FIGS. 1 to 11.

FIG. 1 is a concept diagram for an apparatus for evaluating a human pose using a fixed camera.

Referring to FIG. 1, the conventional apparatus for evaluating a human pose uses a single fixed camera 10 or multiple fixed cameras 10-1 and 10-2, which are attached to a TV or a smartphone.

This conventional apparatus for evaluating a human pose is not capable of accurately detecting all of joints that are important for motion evaluation. That is, depending on the motion, there is an optimal camera orientation for facilitating detection of the position of each joint, but a fixed camera location is only limitedly able to accurately detect all of the joints. Also, when a specific joint is hidden by other body parts or objects, it is difficult to accurately detect the position of the joint. Accordingly, the conventional technologies provide only a partial evaluation result by comparing and evaluating only some joints, the positions of which are capable of being detected, and thus reliability thereof is low.

Figure 2:
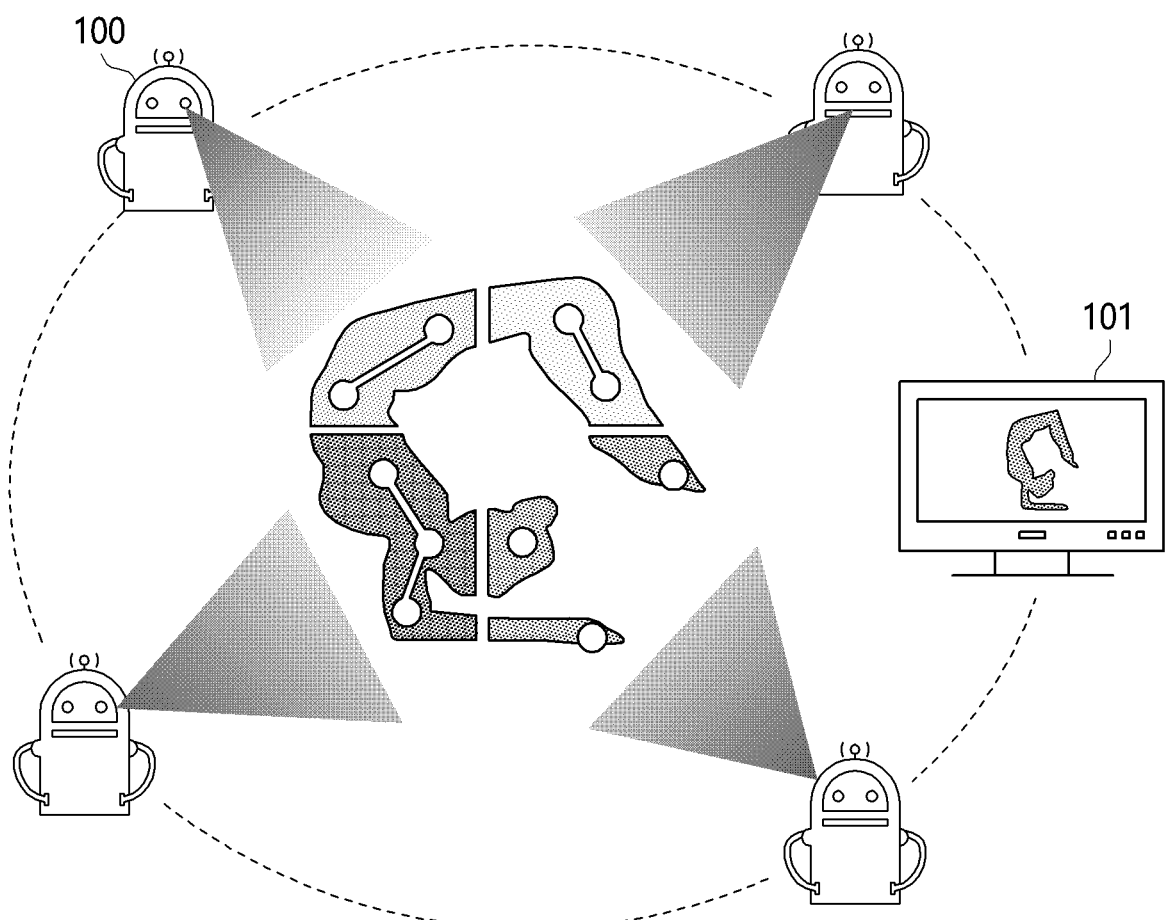
FIG. 2 is a brief concept diagram of an apparatus for evaluating a human motion using a mobile robot according to an embodiment.

FIG. 2 is a brief concept diagram of an apparatus for evaluating a human motion using a mobile robot according to an embodiment.

Referring to FIG. 2, the apparatus 100 for evaluating a human motion using a mobile robot according to an embodiment may be implemented using a mobile robot in which a camera is installed.

This apparatus 100 for evaluating a human motion looks for the optimal location, from which it is possible to accurately extract the positions of joints, and moves thereto by itself, thereby improving the accuracy of detection of joints and ultimately improving the performance of motion evaluation. An embodiment effectively simulates a situation as if a professional trainer were coaching a learner to take an accurate pose while moving to a location at which it is easy to observe the pose of the learner, thereby providing a high-level coaching service.

Here, the apparatus 100 for evaluating a human motion and the mobile robot may be implemented as a single body, or the apparatus 100 for evaluating a human motion may be implemented as a separate device capable of controlling the movement of the mobile robot through wireless communication with the mobile robot and receiving an image captured by the mobile robot.

Hereinafter, an embodiment in which the apparatus 100 for evaluating a human motion is integrated into the mobile robot by being installed therein is illustrated for convenience of description, but the present invention is not limited thereto.

Figure 3:
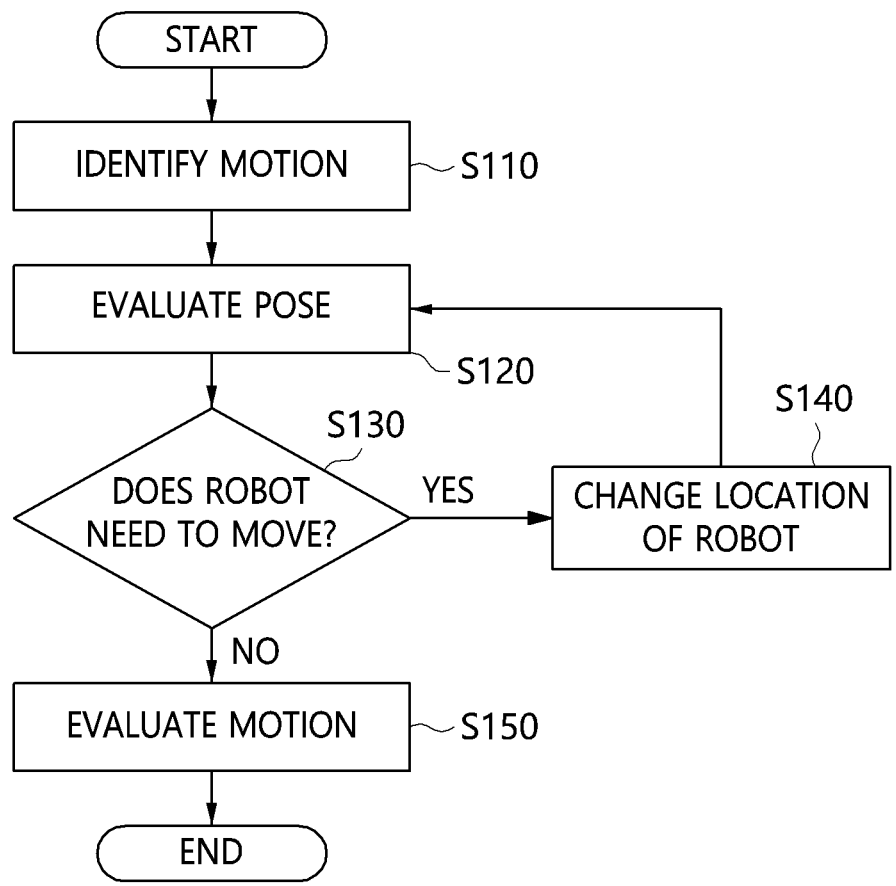
FIG. 3 is a flowchart for explaining a method for evaluating a human motion using a mobile robot according to an embodiment.

FIG. 3 is a flowchart for explaining a method for evaluating a human motion using a mobile robot according to an embodiment.

Referring to FIG. 3, the mobile robot 100 identifies the exercise motion of a user at step S110 based on an image acquired using a camera installed therein.

Here, the exercise motion may be a motion consciously performed by the user to improve his/her health.

The mobile robot 100 analyzes a sequence of images captured from the video acquired using the camera, thereby determining the behavior performed by the user.

Here, the user may perform routine behavior, or may perform an exercise motion, which is the target to be evaluated according to an embodiment.

When the user is performing an exercise motion, rather than routine behavior, the mobile robot 100 identifies the type of the exercise motion.

Here, a specific method for identifying a motion may follow the method described in the patent document titled "method for enabling robot to recognize user-adaptive behavior and apparatus for the same" (Korean Patent Application Publication No. 10-2019-0109364).

Here, the mobile robot 100 retrieves information corresponding to the identified exercise motion from a database in which a standard pose and pose profile for each type of exercise motion are constructed.

Here, the standard pose may be information about a correct pose for an exercise motion.

Here, the pose profile may be meta-information including body segment weight information and optimal observation direction information for each body segment. Here, the body segment weight information may be information about body segments that must be considered important when a standard pose is performed, and the optimal observation direction information for each body segment may be information about the optimal observation direction for accurately evaluating each body segment.

These standard pose and pose profile for each type of exercise motion may be constructed using information acquired from specialists in the corresponding exercise.

The mobile robot 100 compares the pose of the user appearing in the image captured at a certain location with the standard pose of the exercise motion, thereby evaluating the accuracy of the pose at step S120.

Here, the human motion evaluation apparatus 200 extracts an evaluation target body segment from the pose of the user based on the pose profile, evaluates the accuracy of the pose by comparing the evaluation target body segment with the corresponding body segment in the standard pose, and records the evaluated pose accuracy in a pose evaluation chart. A detailed description thereof will be made later with reference to FIG. 4 and FIG. 5.

Then, the mobile robot 100 determines at step S130 whether it is necessary to move to another location. That is, whether the pose is sufficiently evaluated at the current location is determined.

When it is determined at step S130 that it is necessary to move, the mobile robot 100 moves to the next target location at step S140.

Here, the next target location may be a location from which it is advantageous to evaluate the pose. A detailed description of step S140 will be made later with reference to FIGS. 6 to 10.

Through steps S120 to S140, the mobile robot 100 repeats relocation and pose evaluation, and information about the joints and body segments respectively detected and evaluated at each location may be continuously recorded in the pose evaluation chart.

However, when it is determined at step S130 that there is no need to move, the mobile robot 100 provides the final result of user motion evaluation at step S150 by combining the pose evaluation results. That is, when pose evaluation information for all of the body segments illustrated in the pose evaluation chart is obtained, the mobile robot 100 finally evaluates the motion of the user by combining the pose evaluation information that has been acquired up to that point in time.

Here, the final evaluation of the motion is provided as the final pose accuracy score M for all of the body segments, which is calculated using the following Equation (1) based on the weight (w) for each body segment provided in the pose profile, the detection accuracy (j) of the respective joints calculated at step S120, the pose accuracy score (s) of each body segment, and the number of times (n) each body segment is evaluated.

$$M = \frac{\sum_{i=0}^{m} w_i B_i}{\sum_{i=0}^{m} w_i} \quad (1)$$

In Equation (1), m denotes the number of all body segments, and may be, for example, 15, and $B_i$ denotes the final pose accuracy score of the i-th body segment, which is calculated by totaling the pose accuracy scores when the i-th body segment is evaluated n times, and may be calculated using the following Equation (2):

$$B_i = \frac{\sum_{k=1}^{n} s_{i,k} E_{i,k}}{n} \quad (2)$$

In Equation (2), $E_i$ denotes a body segment detection accuracy value calculated using the detection accuracy of joints $j_a$ and $j_b$ at the opposite ends of the i-th body segment, and may be calculated using the following Equation (3):

$$E_i = (j_a + j_b)/2 \quad (3)$$

Hereinbelow, the pose evaluation step (S120) illustrated in FIG. 3 will be described in detail.

Figure 4:
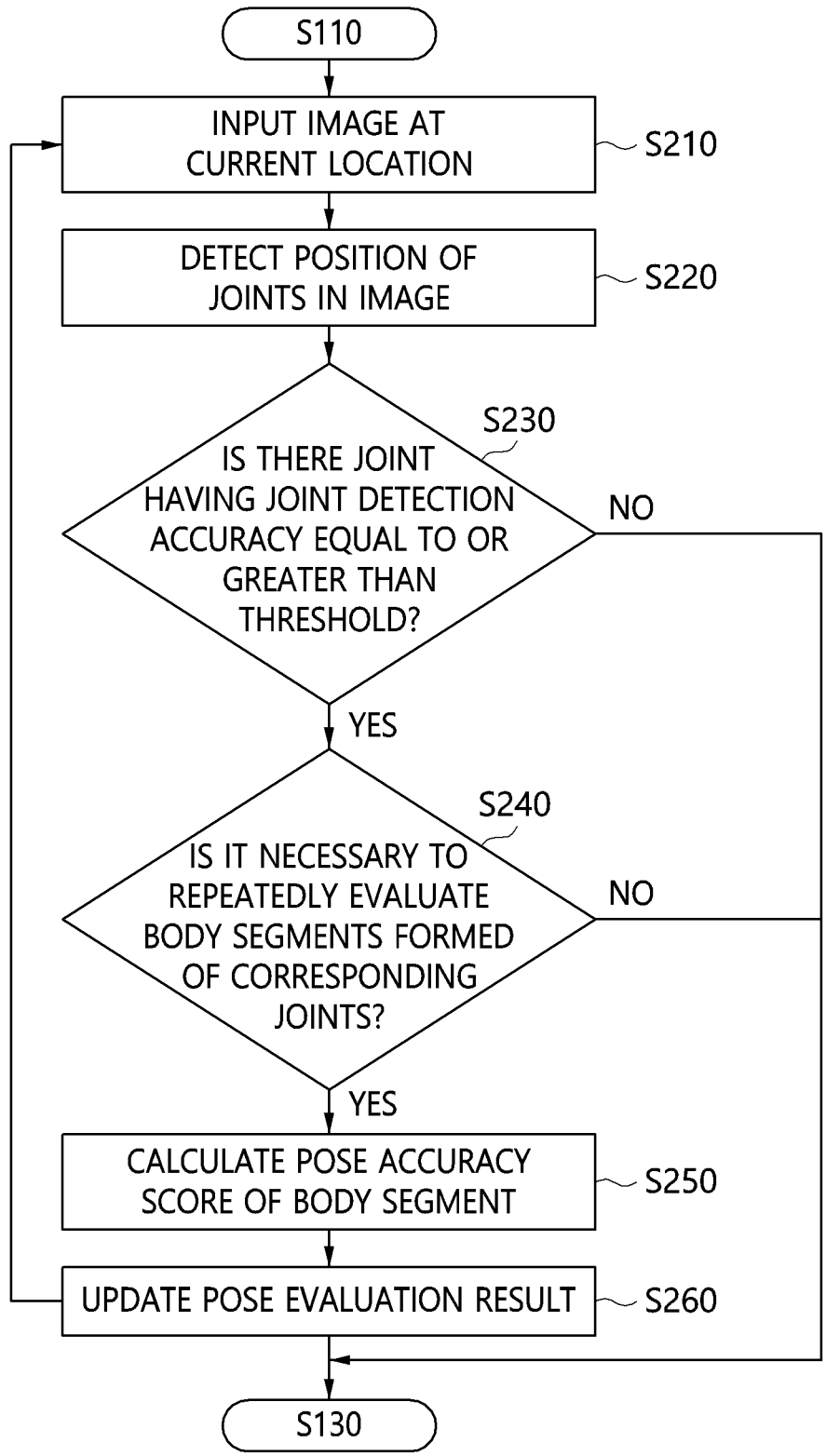
FIG. 4 is a flowchart for explaining a pose evaluation step according to an embodiment.
Figure 5:
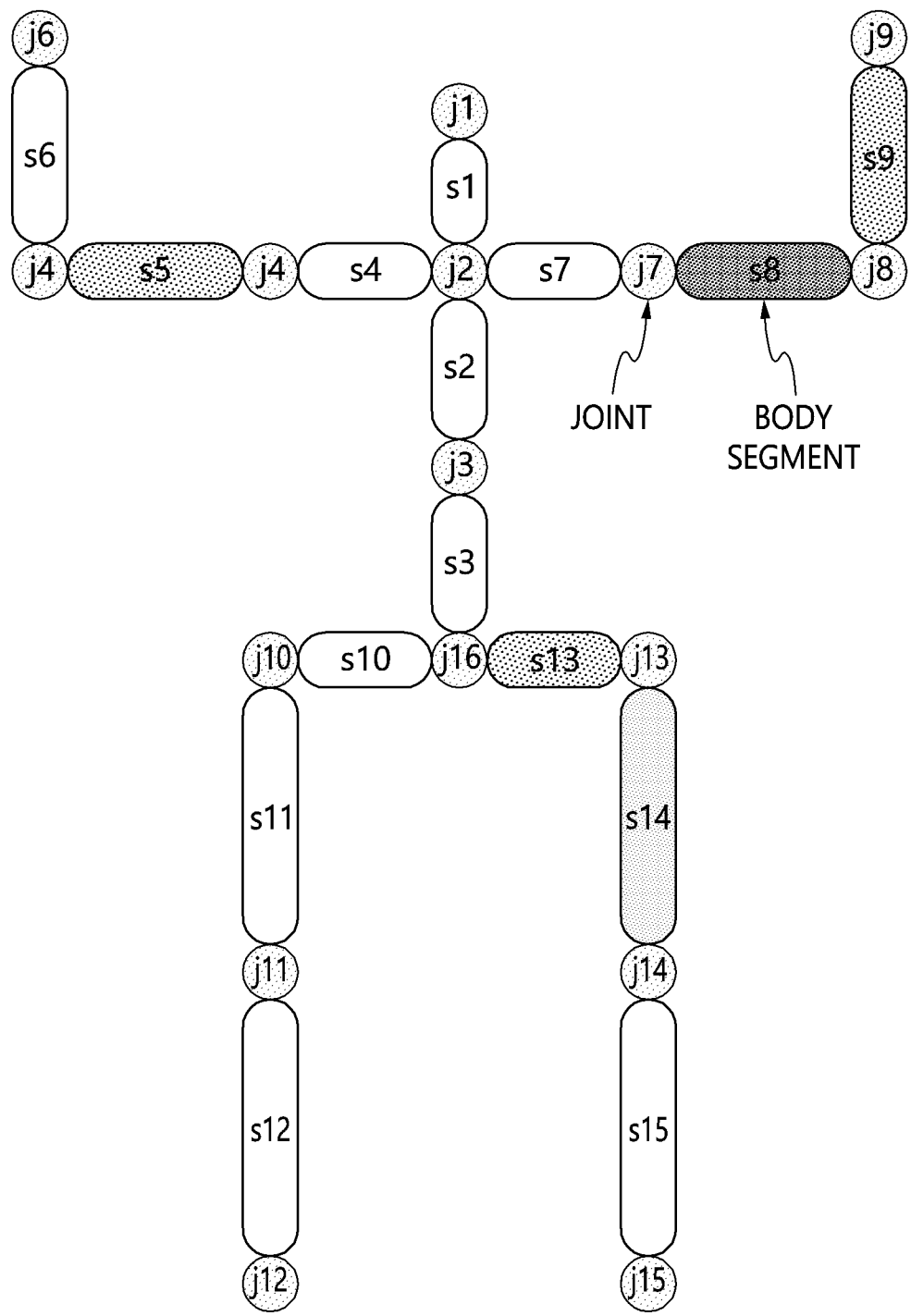
FIG. 5 is an exemplary view of a pose evaluation chart according to an embodiment.

FIG. 4 is a flowchart for explaining a pose evaluation step according to an embodiment, and FIG. 5 is an exemplary view of a pose evaluation chart according to an embodiment.

Referring to FIG. 4, the mobile robot 100 captures an image, including the entire body of a user, at the current location thereof at step S210.

Then, the mobile robot 100 detects the positions of joints in the captured image of the entire body of the user at step S220.

Referring to the pose evaluation chart illustrated in FIG. 5, the joints capable of being detected in an image of an entire human body may be a total of 16 joints from j1 to j16. Also, a total of 15 body segments from s1 to s15 may be formed between the 16 joints.

Here, because joints that are visible rather than being hidden from view in the direction from the mobile robot 100 placed at the current location to the user are capable of being detected in the captured entire body image, the joints have high detection accuracy (certainty). However, because joints that are not visible from the view of the robot are not capable of being detected in the entire body image, the mobile robot 100 must estimate the positions of these joints, and the estimated positions of the joints have low certainty compared to the actually detected positions of the joints.

For example, when the mobile robot 100 is located on the right side of the user, the joints of the right arm and the right leg, which are visible from the view of the robot, have high detection accuracy, but the joints of the left arm and left leg, which are not visible from the view of the robot, have low detection accuracy.

Therefore, according to an embodiment, the mobile robot 100 performs the pose evaluation process only for joints having a detection accuracy equal to or greater than a threshold when viewed from the viewpoint of the robot.

That is, the mobile robot 100 calculates the joint detection accuracy for each of the detected joints, and determines at step S230 whether joints, the calculated detection accuracy of which is equal to or greater than the threshold, are present.

When it is determined at step S230 that joints, the detection accuracy of which is equal to or greater than the threshold, are present, the mobile robot 100 calculates a pose accuracy score only for the body segment formed of the corresponding joints at step S250.

Here, a body segment may be evaluated one or more times.

Therefore, the mobile robot 100 further performs step S240 in order to determine whether it is necessary to repeat evaluation of the body segment formed of the detected joints, the detection accuracy of which is equal to or greater than the threshold. That is, whether evaluation of the body segment has been sufficiently repeated is determined.

Accordingly, when it is determined at step S240 that it is necessary to repeatedly evaluate the body segment formed of the corresponding joints, the mobile robot 100 calculates the pose accuracy score of the corresponding body segment at step S250 and updates the evaluation result at step S260 when the pose accuracy score is calculated.

Then, when the pose accuracy score of the body segment is calculated, the mobile robot 100 updates the evaluation result at step S260.

Here, the pose accuracy score may be recorded/updated in the pose evaluation chart illustrated in FIG. 5.

Here, the detection accuracy of the joints, the pose accuracy score of the body segment, and the number of times the body segment is evaluated, which are information calculated by the above-described pose evaluation process, may be recorded in the pose evaluation chart.

Here, because the same joint or the same body segment can be evaluated multiple times, all the information that is calculated every time evaluation is performed may be recorded.

Here, the number of times evaluation is performed may be expressed using a brightness or color difference.

For example, referring to FIG. 5, a value of the brightness expressed in a joint or body segment may be proportional to the number of times evaluation is performed. That is, it may be assumed that the body segment s4 is not evaluated, the body segment s14 is evaluated once, the body segment s5 is evaluated twice, and the body segment s8 is evaluated three times.

This pose evaluation chart may be used as an interface for providing information about the current progress of evaluation to the user.

Meanwhile, referring again to FIG. 4, when it is determined at step S230 or S240 that joints, the detection accuracy of which is equal to or greater than the threshold, are not present at the current location or that such joints are present but the body segment formed of the corresponding joints has been sufficiently evaluated because the number of times evaluation has been performed is equal to or greater than a preset number, the mobile robot 100 moves to the next location at step S130.

Hereinbelow, the robot relocation step (S140) illustrated in FIG. 3 will be described in detail.

Figure 6:
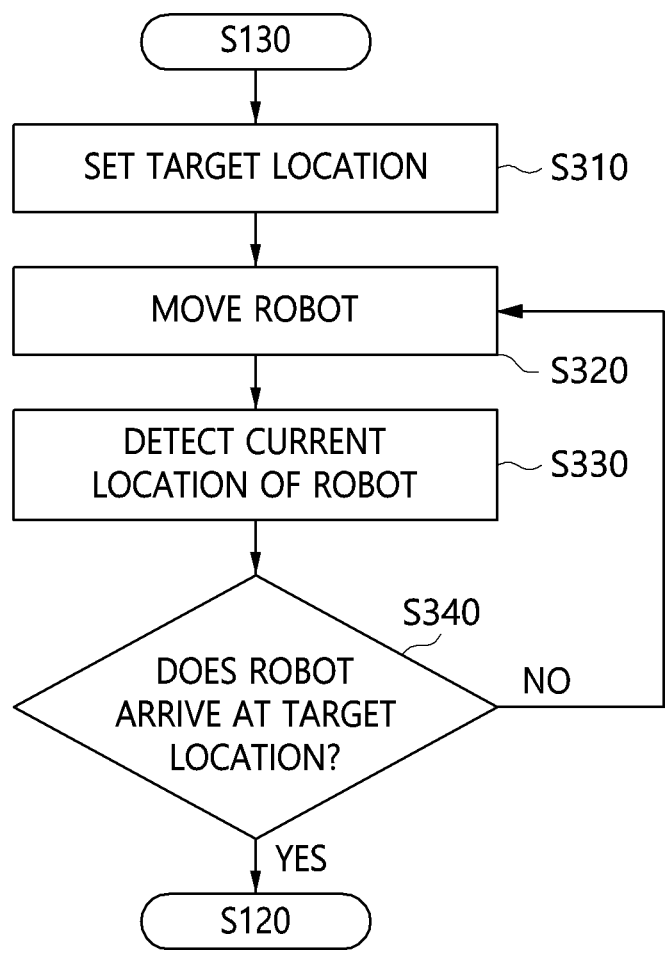
FIG. 6 is a flowchart for explaining a robot relocation step according to an embodiment.
Figure 7:
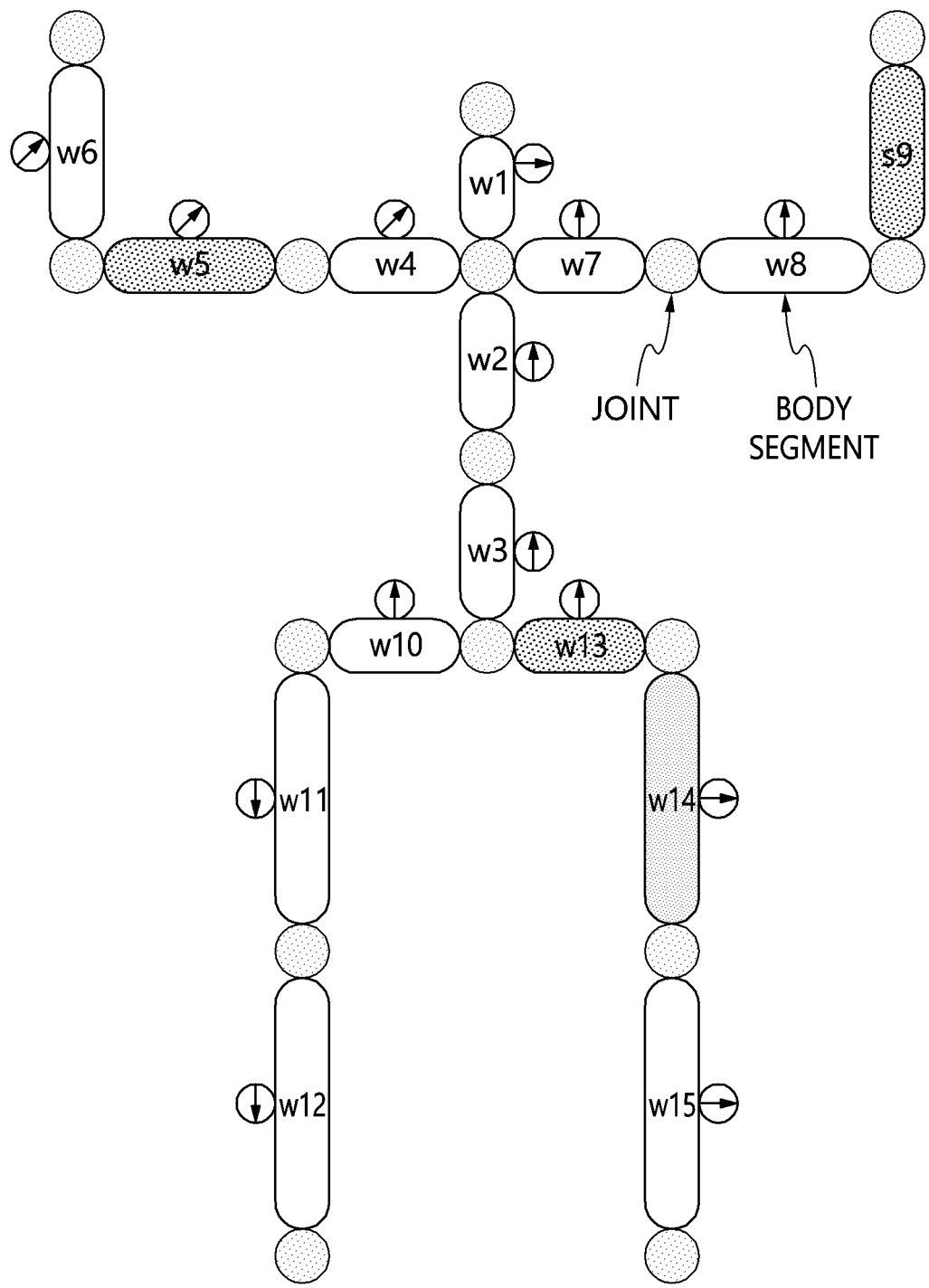
FIG. 7 is an exemplary view of a pose profile for setting a target location according to an embodiment.
Figure 8:
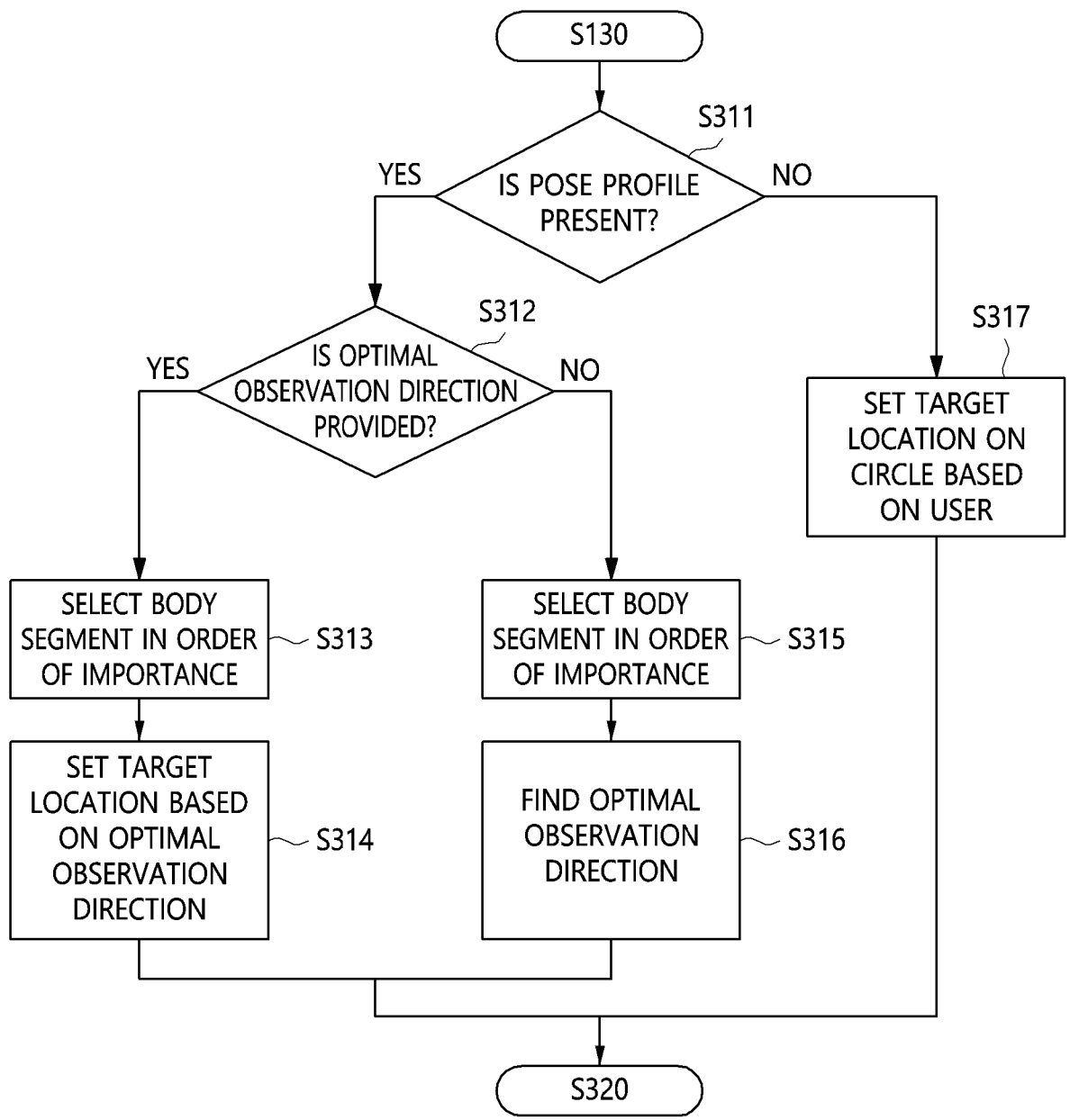
FIG. 8 is a flowchart for explaining the step of setting a target location according to an embodiment.
Figure 9:
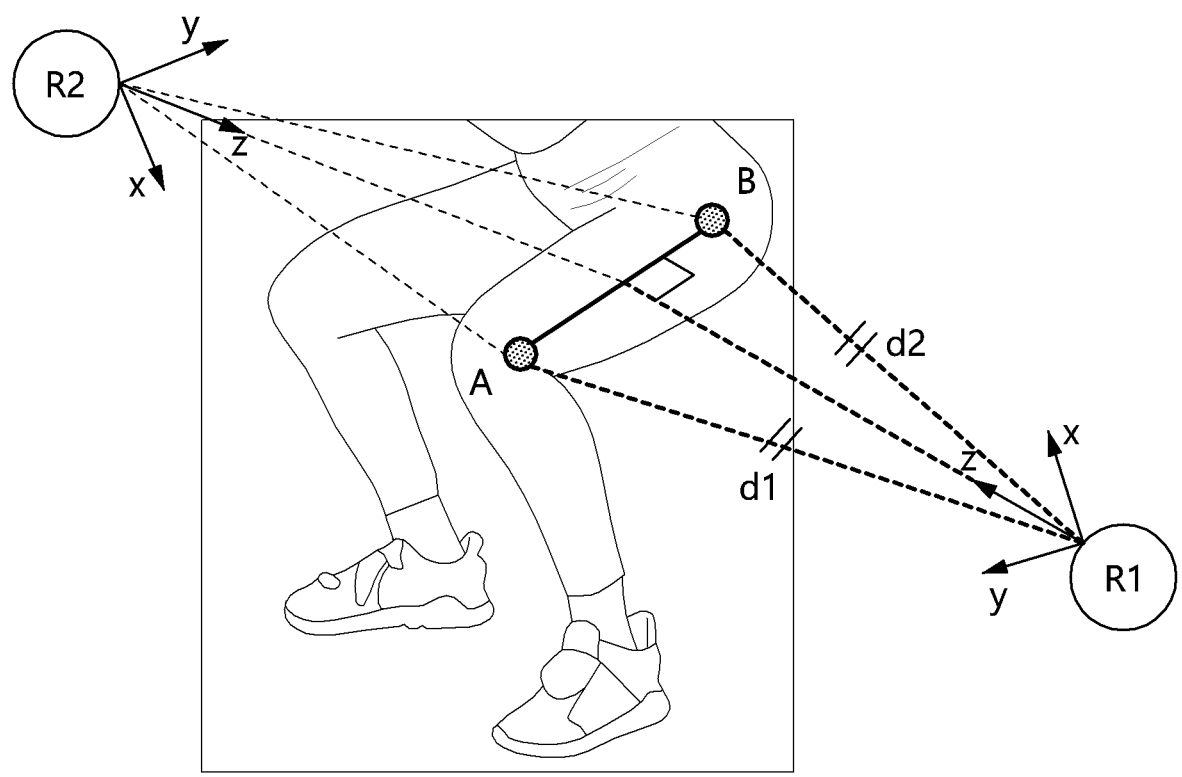
FIG. 9 is an exemplary view for explaining a method for searching for the optimal direction from which to observe a body segment according to an embodiment.
Figure 10:
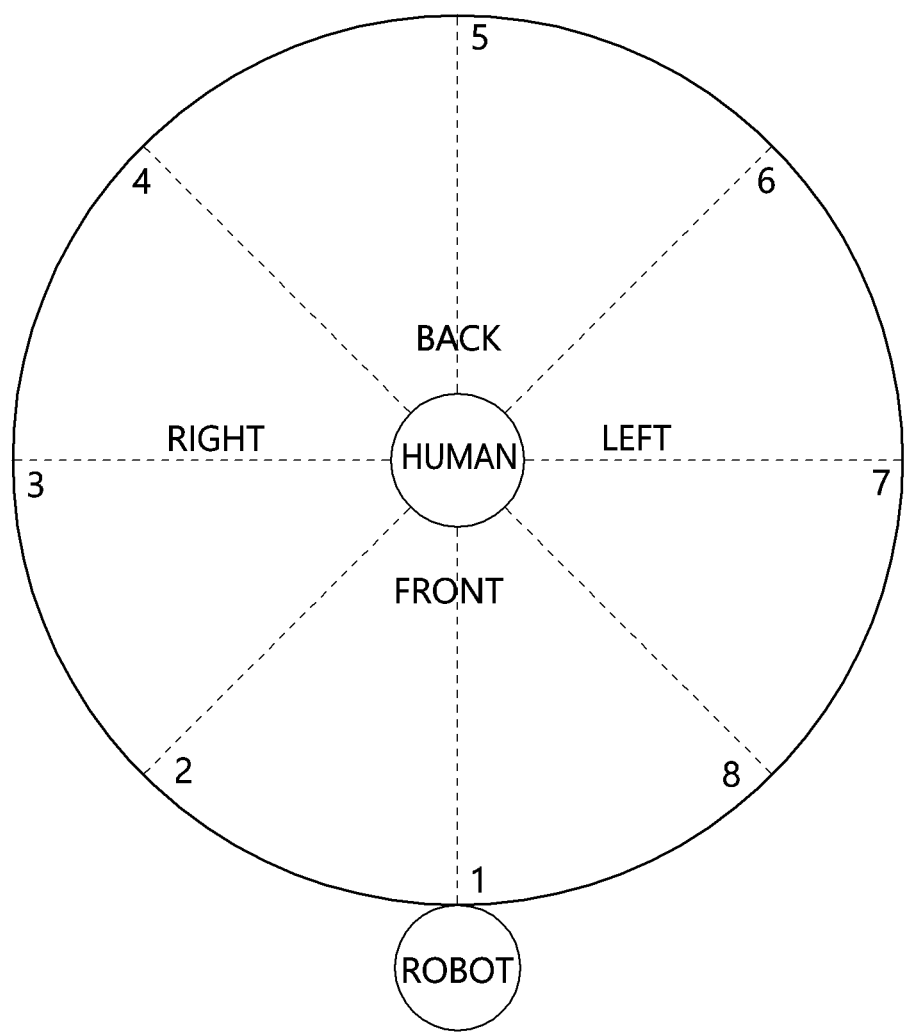
FIG. 10 is an exemplary view illustrating that the target location of a mobile robot is decided on when no pose profile is provided according to an embodiment.

FIG. 6 is a flowchart for explaining a robot relocation step according to an embodiment, FIG. 7 is an exemplary view of a pose profile for setting a target location according to an embodiment, FIG. 8 is a flowchart for explaining the step of setting a target location according to an embodiment, FIG. 9 is an exemplary view for explaining a method for searching for the optimal direction from which to observe a body segment according to an embodiment, and FIG. 10 is an exemplary view illustrating that the target location of a mobile robot is decided on when no pose profile is provided according to an embodiment.

Referring to FIG. 6, the mobile robot 100 sets the next target location to move to at step S310.

Here, the target location may be a favorable location from which to evaluate a pose.

Here, setting the target location may be performed using any of various methods depending on whether a pose profile is present.

Here, the pose profile may include a weight value, indicating the importance of each body segment when a specific pose is evaluated, and a 2D direction vector, which represents a direction from which it is easy to evaluate each body segment. For example, referring to FIG. 7, weights w1, w2, . . . , w15 and 2D direction vectors are marked on the respective body segments drawn in a pose profile.

Such a pose profile may be acquired from a specialist in the corresponding exercise motion, and this is because the specialist in the domain is well aware of which body segment is most important to take the pose and the optimal observation direction information for evaluating the body segment based on his/her experience.

For example, when specialists in the domain determine that the body segments of the calves and thighs are most important and that the position of the spine is second most important when holding a squat position, weights for the corresponding body segments may be set high depending on the importance thereof. On the other hand, because the positions of the arms are less important, weights for the corresponding body segment may be set low, and a weight for a body segment that is not important may be set to '0'. Also, the distance between the two legs, which is an important evaluation factor for the squat position, can be most easily checked when viewed from the front, and the knee flexion angle and whether the spine is kept straight can be evaluated most accurately when viewed from the side.

Because such domain knowledge possessed by specialists in the domain can be easily edited without expense using a user interface for a pose profile, it may be easily provided.

However, in an embodiment, considering the situation in which no pose profile information is provided, a target location may be set depending on whether information provided in the pose profile is present or on whether the optimal observation direction is included in the pose profile.

Specifically, referring to FIG. 8, the mobile robot 100 determines whether a pose profile is present at step S311.

When it is determined at step S311 that a pose profile is present, the mobile robot 100 determines at step S312 whether an optimal observation direction is provided in the pose profile.

When it is determined at steps S311 and S312 that the importance of each body segment and optimal observation direction information are provided in the pose profile, the mobile robot 100 evaluates body segments in order of importance, which is the most important information for deciding on the target location to which the robot is to move, at step S313, in which case the target location is set based on the optimal observation direction information for each body segment provided in the pose profile at step S314.

However, when it is determined at step S311 or S312 that only the importance of each body segment is provided in the pose profile, the mobile robot 100 evaluates body segments in order of importance at step S315, but because no optimal observation direction information is provided, it is necessary to look for a location from which the body segment can be most clearly observed, that is, the optimal observation location, at step S316.

As shown in FIG. 9, it may be assumed that the left thigh, which is the body segment AB formed of the joints A and B, is evaluated in order to evaluate a specific pose. Here, the optimal location for the robot to evaluate the body segment AB is the location at which the following two conditions are satisfied.

First, the optimal observation location must be a location from which the joint A and the joint B can be most accurately detected. As described above, joint detection accuracy is very important for evaluating a pose. Therefore, it must be possible to detect joint A and joint B with high accuracy, and thus the same must be readily visible rather than hidden.

Second, from the location, it must be possible for the robot to best observe the angle made by the body segment AB. A specific pose is evaluated based on a set of angles made by the respective body segments of a user when the user takes the pose and on a set of angles made by the corresponding body segments in a standard pose. Therefore, selecting a location from which the angle made by the body segment is capable of being accurately measured is as important as the accurate detection of joints.

The location of the robot satisfying both of the above-described conditions is the point at which the following three conditions are simultaneously satisfied.

① The point at which both points A and B are observed in an image captured by the robot ② The point at which the line segment AB, the endpoints of which are the points A and B in a 3D space, is perpendicular to the z-axis of a 3D coordinate system having the robot (specifically, the camera of the robot) as the origin thereof ③ The point at which the actual measurement of the distance d1 from the robot to the point A in the z direction is equal to the actual measurement of the distance d2 from the robot to the point B in the z direction In FIG. 9, the location of the mobile robot satisfying all of the above-described three conditions may be R1. In the 2D image formed of an x-y plane captured by the mobile robot placed at the location R1, all of the joints A and B can be observed. Also, this point is the point at which the body segment AB is perpendicular to the z-axis of the mobile robot and at which the distance from the mobile robot to the joint A is equal to the distance from the mobile robot to the joint B.

Therefore, the location R1 satisfying all of the above-described three conditions may be set as the optimal observation point at which joints can be best detected and from which the angle made by the body segment can be best observed.

Meanwhile, the location R2 satisfies the conditions ② and ③, but does not satisfy the condition ① because the body segment AB is hidden by the right thigh of the user, and thus it is not the optimal location to move to.

However, it is not easy to find a point satisfying the above-described conditions ② and ③ when the mobile robot is operating. Therefore, in an embodiment, the condition ②, in which the angle made by the line segment AB and the z-axis must be 90 degrees, is relaxed, and a designated range (90 degrees±α) may be used. Also, the condition ③, in which d1 must be equal to d2, is relaxed, and a designated distance difference range (|d1−d2|<α) may be used.

Meanwhile, when a specific pose is taken, there may be multiple optimal locations for observing each body segment depending on the circumstances. In this case, the target location that is closest to the current location of the robot may be set as the next location of the robot.

Referring again to FIG. 8, when it is determined at step S311 that no pose profile is provided, the mobile robot 100 determines that all of the body segments have the same importance. Accordingly, the mobile robot 100 sets a circle drawn at a fixed distance from the user and sets a point on the circle, acquired by dividing the circle into sectors according to a fixed angle, as the target location at step S317 such that the mobile robot 100 can capture an image of the entire body of the user. For example, referring to FIG. 10, the mobile robot 100 may repeatedly evaluate a pose from eight locations by sequentially moving thereto while maintaining a fixed distance from the user.

Referring again to FIG. 6, the mobile robot 100 moves to the target location thereof at step S320 by controlling the hardware driver unit of the robot. Here, the robot may move while maintaining a certain distance from the user such that an image of the entire body of the user can be captured.

The mobile robot 100 determines whether it has arrived at the target location by repeatedly identifying the current location thereof during movement at step S330. The mobile robot 100 may repeatedly perform steps S320 and S330 until it determines that it has arrived at the target location at step S340.

Meanwhile, when it is determined at step S340 that the robot has arrived at the target location, a pose evaluation process at step S120 (illustrated in FIG. 4) is performed.

Figure 11:
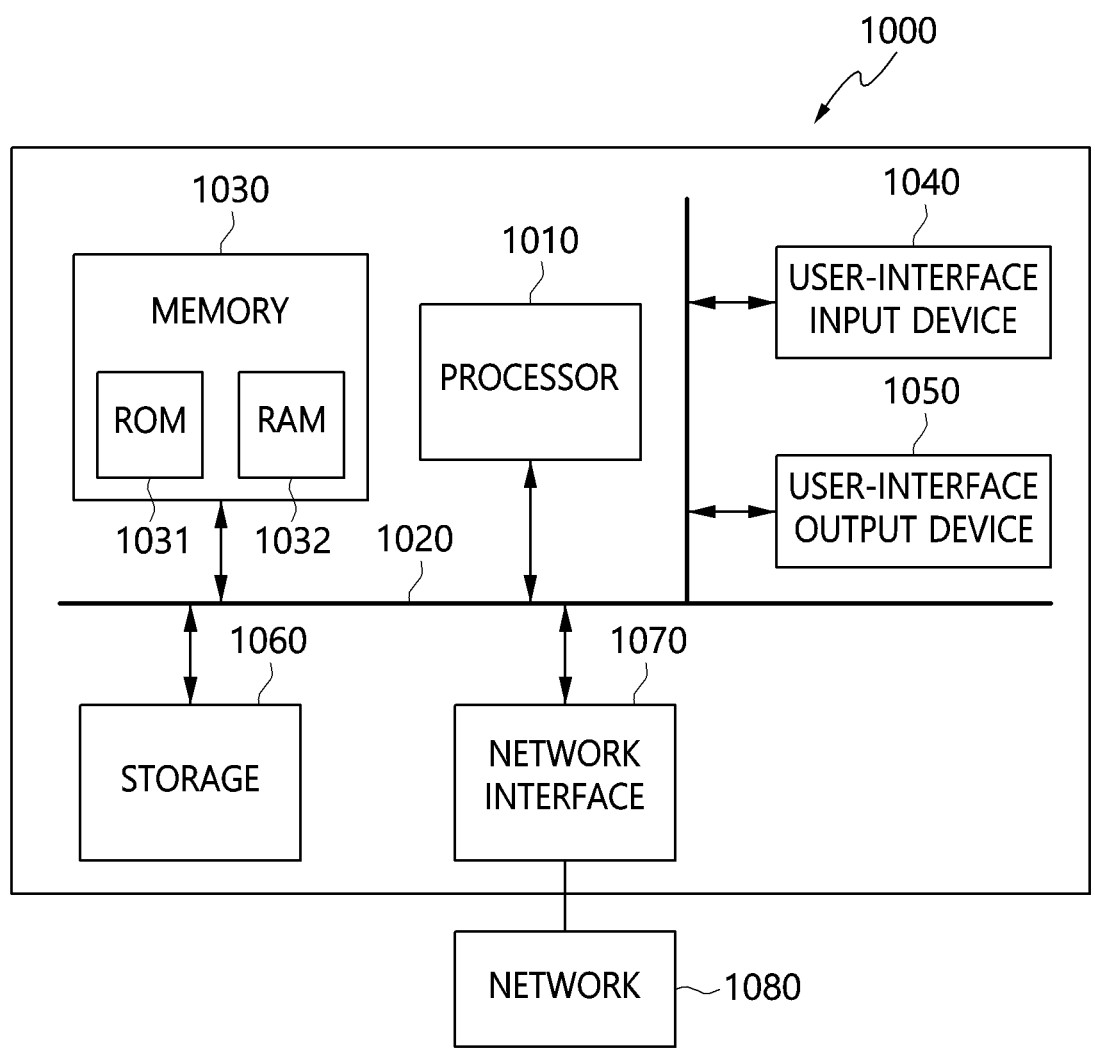
FIG. 11 is a view illustrating a computer system configuration according to an embodiment.

FIG. 11 is a view illustrating a computer system configuration according to an embodiment.

The apparatus for evaluating a human pose using a mobile robot according to an embodiment may be implemented in a computer system 1000 including a computer-readable recording medium.

The computer system 1000 may include one or more processors 1010, memory 1030, a user-interface input device 1040, a user-interface output device 1050, and storage 1060, which communicate with each other via a bus 1020. Also, the computer system 1000 may further include a network interface 1070 connected with a network 1080. The processor 1010 may be a central processing unit or a semiconductor device for executing a program or processing instructions stored in the memory 1030 or the storage 1060. The memory 1030 and the storage 1060 may be storage media including at least one of a volatile medium, a non-volatile medium, a detachable medium, a non-detachable medium, a communication medium, and an information delivery medium. For example, the memory 1030 may include ROM 1031 or RAM 1032.

According to the embodiment, when a user performs a specific motion, a mobile robot moves, by itself, to the optimal location from which to detect the positions of joints and observes the motion of the user from different directions, whereby there is an advantage in that the reliability of evaluation of a pose or motion may be significantly improved.

Although the embodiments of the present invention have been described with reference to the accompanying drawings, those skilled in the art will appreciate that the present invention may be practiced in other specific forms without changing the technical spirit or essential features of the present invention. Therefore, the embodiments described above are illustrative in all aspects and should not be understood as limiting the present invention.

What is claimed is:

1. A method performed by an apparatus for evaluating a human motion using a mobile robot, the apparatus including a processor and a memory operably coupled to the processor, wherein the memory stores program instructions to be executed by the processor; and the method comprising:
    identifying performed by the processor, an exercise motion of a user by analyzing an image of an entire body of the user captured using a camera installed in the mobile robot and detecting a standard pose and a pose profile of the identified exercise motion;
    evaluating, performed by the processor, a pose of the user by comparing the standard pose of the identified exercise motion with images of the entire body of the user captured by the camera of the mobile robot from two or more target locations; and
    comprehensively evaluating, performed by the processor, the exercise motion of the user based on pose evaluation information of the user from each of the two or more target locations,
wherein the pose profile includes a weight value, indicating the importance of each body segment when a specific pose is evaluated,
wherein the target location is set based on the optimal observation direction information for each body segment which are selected based on the weight value in the pose profile,
wherein evaluating the pose of the user is configured to repeatedly evaluate each body segment, and
wherein evaluating exercise motion of the user comprises:
    calculating a detection accuracy value of a body segment using an average of detection accuracy values of joints forming the body segment;
    calculating a final pose accuracy score of the body segment using a body segment detection accuracy score and an average of the detection accuracy values of the body segment; and
    calculating a final motion accuracy based on the final pose accuracy score and a weight of each body segment.

2. The method of claim 1, wherein evaluating the pose of the user comprises:
    detecting a joint in the images of the entire body of the user; and
    calculating a pose accuracy score for a body segment formed of joints, a detection accuracy value of which is equal to or greater than a threshold.

3. The method of claim 2, wherein evaluating the pose of the user further comprises:
    recording the detection accuracy value of the joint and the pose accuracy score for the body segment in a pose evaluation chart,
    wherein, in the pose evaluation chart, all of body segments and joints of the user are marked.

4. The method of claim 3, wherein:
    evaluating the pose of the user is configured to repeatedly evaluate each body segment, and
    recording the detection accuracy value and the pose accuracy score is configured to record a number of times the body segment is evaluated in the pose evaluation chart using a color or brightness such that the number of times is identified according to the color or brightness.

5. The method of claim 2, wherein:
    evaluating the pose of the user is configured to set the target locations based on a pose profile, and
    when the pose profile further includes a 2D direction vector for each body segment, a body segment to be observed next is selected in order of weight, and the target location, which is an optimal location from which to observe the selected body segment, is set based on the 2D direction vector of the selected body segment.

6. The method of claim 2, wherein:
    evaluating the pose of the user is configured to set the target locations based on a pose profile,
    when the pose profile includes only a weight for each body segment, a body segment to be observed next is selected in order of weight, and the target location, which is an optimal location from which to observe the selected body segment, is calculated in real time, and
    the target location is set to a point from which two joints forming the selected body segment are capable of being observed and at which distances from the two joints are equal to each other, the point being extended from a center of the body segment so as to be perpendicular to the body segment.

7. The method of claim 2, wherein:
    evaluating the pose of the user is configured such that, when no pose profile is provided, the target location is set while moving to points at a fixed distance from the user by a fixed angle.

8. An apparatus for evaluating a human motion using a mobile robot, comprising:
    memory in which at least one program is recorded; and
    a processor for executing the program,
    wherein the program performs
        identifying an exercise motion of a user by analyzing an image of an entire body of the user captured using a camera installed in the mobile robot and detecting a standard pose and a pose of the identified exercise motion;
        evaluating a pose of the user by comparing the standard pose of the identified exercise motion with images of the entire body of the user captured by the camera of the mobile robot from two or more target locations; and
        comprehensively evaluating the exercise motion of the user based on pose evaluation information of the user from each of the two or more target locations,
    wherein the pose profile includes a weight value, indicating the importance of each body segment when a specific pose is evaluated,
    wherein the target location is set based on the optimal observation direction information for each body segment which are selected based on the weight value in the pose profile,
    wherein evaluating the pose of the user is configured to repeatedly evaluate each body segment, and
    wherein evaluating the exercise motion of the user comprises:
        calculating a detection accuracy value of a body segment using average of detection accuracy values of joints forming the body segment;
        calculating a final pose accuracy score of the body segment using a body segment detection accuracy score and an average detection accuracy values of the both, segment; and
        calculating final motion accuracy based on the pose accuracy score and a weight of body segment.

9. The apparatus of claim 8, wherein evaluating the pose of the user comprises:
    detecting a joint in the images of the entire body of the user; and
    calculating a pose accuracy score for a body segment formed of joints, a detection accuracy value of which is equal to or greater than a threshold.

10. The apparatus of claim 9, wherein evaluating the pose of the user further comprises:
recording the detection accuracy value of the joint and the pose accuracy score for the body segment in a pose evaluation chart,
wherein, in the pose evaluation chart, all of body segments and joints of the user are marked.

11. The apparatus of claim 10, wherein:
evaluating the pose of the user is configured to repeatedly evaluate each body segment, and
recording the detection accuracy value and the pose accuracy score is configured to record a number of times the body segment is evaluated in the pose evaluation chart using a color or brightness such that the number of times is identified according to the color or brightness.

12. The apparatus of claim 9, wherein:
evaluating the pose of the user is configured to set the target locations based on a pose profile, and
when the pose profile further includes a 2D direction vector for each body segment, a body segment to be observed next is selected in order of weight, and the target location, which is an optimal location from which to observe the selected body segment, is set based on the 2D direction vector of the selected body segment.

13. The apparatus of claim 9, wherein:
evaluating the pose of the user is configured to set the target locations based on a pose profile,
when the pose profile includes only a weight for each body segment, a body segment to be observed next is selected in order of weight, and the target location, which is an optimal location from which to observe the selected body segment, is calculated in real time, and
the target location is set to a point from which two joints forming the selected body segment are capable of being observed and at which distances from the two joints are equal to each other, the point being extended from a center of the body segment so as to be perpendicular to the body segment.

14. The apparatus of claim 9, wherein:
evaluating the pose of the user is configured such that, when no pose profile is provided, the target location is set while moving to points at a fixed distance from the user by a fixed angle.

15. A method performed by an apparatus for evaluating a human motion using a mobile robot,
the apparatus including a processor and a memory operably coupled to the processor, wherein the memory stores program instructions to be executed by the processor, and
the method comprising:
identifying, performed by the processor, an exercise motion of a user by analyzing an image of an entire body of the user captured using a camera installed in the mobile robot;
detecting, performed by the processor, a standard pose and a pose profile of the identified exercise motion;
setting, performed by the processor, a target location based on the pose profile;
evaluating, performed by the processor, a pose of the user by comparing the standard pose with an image of the entire body of the user that is captured by the camera after the mobile robot moves to the set target location; and
comprehensively evaluating, performed by the processor, the exercise motion of the user based on pose evaluation information of the user from each of the target locations,
wherein setting the target location and evaluating the pose of the user are repeatedly performed
wherein the pose profile includes a weight value, indicating the importance of each body segment when a specific pose is evaluated,
wherein the target location is set based on the optimal observation direction in information for each body segment which are selected based on the weight value in the pose profile,
wherein evaluating the pose of the user is configured to repeatedly evaluate each body segment, and
wherein evaluating the exercise motion of the user comprises:
calculating a detection accuracy value of a both segment using an as average of detection accuracy values of joints forming the body segment;
calculating a final pose accuracy score of the body segment using a body segment detection accuracy score and an average of the detection accuracy values of the body segment; and
calculating a final motion accuracy based on the final pose accuracy score and a eight of each body segment.

16. The method of claim 15, wherein evaluating the pose of the user comprises:
detecting a joint in the image of the entire body of the user; and
repeatedly calculating a pose accuracy score for a body segment formed of joints, a detection accuracy value of which is equal to or greater than a threshold, as many times as a predetermined evaluation number.

17. The method of claim 15, wherein:
setting the target location is configured to set the target location based on the pose profile, and
when the pose profile further includes a 2D direction vector for each body segment, a body segment to be observed next is selected in order of weight, and the target location, which is an optimal location from which to observe the selected body segment, is set based on the 2D direction vector of the selected body segment.

18. The method of claim 15, wherein:
setting the target location is configured to set the target location based on the pose profile,
when the pose profile includes only a weight for each body segment, a body segment to be observed next is selected in order of weight, and the target location, which is an optimal location from which to observe the selected body segment, is calculated in real time, and
the target location is set to a point from which two joints forming the selected body segment are capable of being observed and at which distances from the two joints are equal to each other, the point being extended from a center of the body segment so as to be perpendicular to the body segment.

* * * * *